(12) United States Patent
Gorfinkel et al.

(10) Patent No.: US 6,497,804 B1
(45) Date of Patent: *Dec. 24, 2002

(54) METHOD AND APPARATUS FOR DNA SEQUENCING

(75) Inventors: Vera Gorfinkel, Stony Brook, NY (US); Mikhail Gouzman, Lake Grove, NY (US); Luryi Serge, Old Field, NY (US)

(73) Assignee: Research Foundation of the State University of New York, Stony Brook, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/454,093

(22) Filed: Dec. 3, 1999

Related U.S. Application Data

(60) Provisional application No. 60/110,714, filed on Dec. 3, 1998.

(51) Int. Cl.[7] .............................. C02F 1/40; C02F 11/00; C25B 11/00; C25B 13/00; C25B 9/00; G01N 27/403; G01N 27/453
(52) U.S. Cl. .......................................... 204/603; 435/6
(58) Field of Search ............................... 204/603; 435/6

(56) References Cited

U.S. PATENT DOCUMENTS

| | | | | |
|---|---|---|---|---|
| 4,811,218 A | * | 3/1989 | Hunkapiller et al. | 204/461 |
| 5,483,075 A | * | 1/1996 | Smith et al. | 204/461 |
| 5,584,982 A | * | 12/1996 | Dovichi et al. | 204/452 |
| 5,741,412 A | * | 4/1998 | Dovichi et al. | 204/453 |
| 5,784,152 A | * | 7/1998 | Heffelfinger et al. | 250/458.1 |
| 5,784,157 A | * | 7/1998 | Gorfinkel et al. | 204/452 |
| 5,790,727 A | * | 8/1998 | Dhadwal et al. | 204/452 |
| 6,038,023 A | * | 3/2000 | Carlson et al. | 356/326 |
| 6,084,667 A | * | 7/2000 | Melman et al. | 356/246 |
| 6,143,153 A | * | 11/2000 | Middendorf et al. | 204/451 |

* cited by examiner

*Primary Examiner*—Jill Warden
*Assistant Examiner*—Jennine Brown
(74) *Attorney, Agent, or Firm*—F. Chau & Associates, LLP

(57) ABSTRACT

The development of the network structure and the basic modules of an automated 4-color DNA sequencing apparatus comprising more than one thousand capillary electrophoresis lanes is disclosed. The basic modules represent small 32-lane units based on multicolor excitation of fluorescent labels and single-photon detection. The individual units operate asynchronously, controlled by a network computer. Excitation of fluorescence is done with low-power illumination via a fiber-optic network.

13 Claims, 5 Drawing Sheets

DNA loading into capillary bundle

Loading DNA samples from multilayer chip

Bundles of different configurations
Split bundles

Monolithic bundles front view    back view

US 6,497,804 B1

METHOD AND APPARATUS FOR DNA SEQUENCING

CROSS-REFERENCE TO RELATED APPLICATIONS

This application claims priority to Provisional Application Serial No. 60/110,714 filed Dec. 3, 1998 and incorporated herein by reference.

GOVERNMENTAL INFORMATION

The U.S. Government has a license in this invention and the right in limited circumstances to require the patent owner to license others on reasonable terms of grant number HG01487 awarded by the National Institute of Health (NIH).

TECHNICAL FIELD

The present invention relates to a method and apparatus for DNA sequencing of DNA samples.

BACKGROUND

A basic engineering principle that underlies our approach to the implementation of a kilo-lane sequencer is the absence of scanning. Scanning of a laser beam implies inefficient use of the illumination power and a significant waste of the valuable information. Clearly, an optimum detection system must be observing the DNA zones for the entire period of their passage through the observation window to take full advantage of the available information. On the other hand, delivery of illumination to each capillary lane individually by fiber-optic means is also wasteful of optical power and limits the number lanes that could be illuminated by a single laser.

Therefore, a need exists for a system and method which avoids both of these critical inefficiencies.

SUMMARY

By the present invention, the laser power is distributed over fiber-optic networks to 32-lane modular units, where each unit is illuminated in parallel by a focused radiation from the same fiber. To this effect, an important advance achieved in our current work is the demonstration of excellent wave-guiding properties in a planar assembly of rectangular capillaries. In contrast to cylindrical capillaries, an assembly of capillaries of a square cross-section permits a rather uniform illumination of the entire 32-capillary assembly from one edge (Sect. 4.2.3). The novel approach to the implementation of kilo-lane sequencing instruments: the dual-network modular architecture.

DETAILED DESCRIPTION OF PREFERRED EMBODIMENTS

Figure 1:
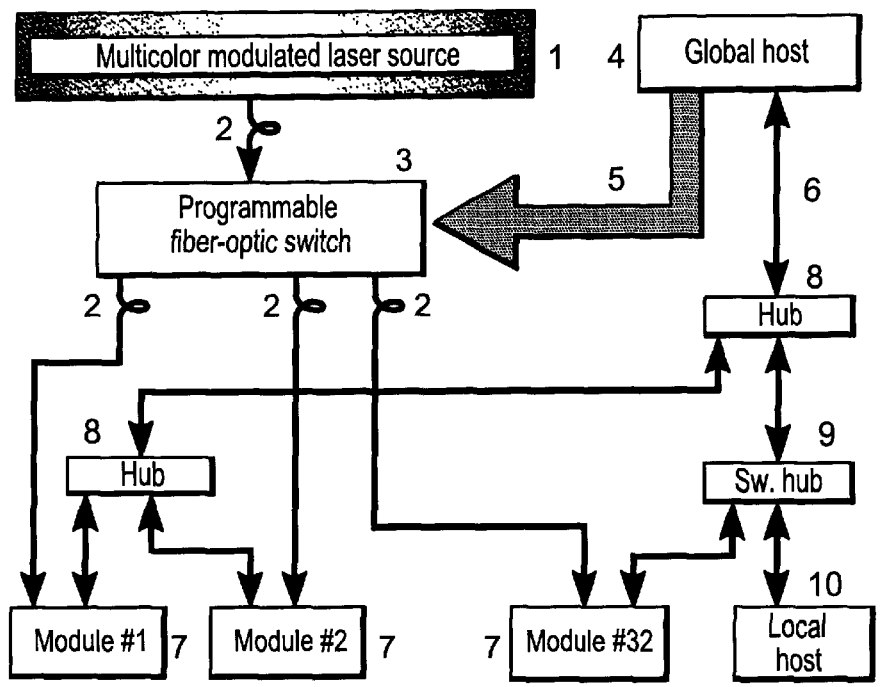
FIG. 1 is a block diagram of the asynchronous kilo-lane DNA sequencing instrument in accordance with the present invention.

Commercially available machines employ either slab gel (ABI-377) or capillary format (ABI-310, CEQ-200, and soon-to-come ABI-3700). By the next year, one can expect the 96-capillary ABI-3700 to hit the market. This will be the highest number of lanes available in any machine. At the same time, several groups are developing new high-throughput sequencing machines, based on integrated technologies, and prepare to overcome the 1,000 channel barrier. Thus, the group of J. W. Balch (Lawrence Livermore National Lab) is developing a 384 channel machine based on micro-channels etched in glass plates with a glass cover. The group of N. J. Dovichi (University of Alberta) is developing a 576 capillary system. DNA sequencing on the basis of micro-fabricated chips has been reported by the group of R. Mathies (University of California, Berkeley).

As far as we are aware, all current development designs of kilo-lane machines conceptually represent scaled up versions of the present sequencer architectures in that they are designed for synchronous operation of all lanes simultaneously. The fluorescence is excited in all lanes simultaneously (or in a multiplexed regime) and the readout uses, typically, CCD arrays or single PMT scanning. Processing and analysis of the data is performed by a powerful computer, often after the sequencing run. The current architecture has certain drawbacks, such as:

Simultaneous loading of 1,000 channels is difficult (requires very expensive micro-loaders) and may lead to lower overall throughput;

Synchronous operation of many channels requires exceptional machine reliability as it may not be forgiving of failures in individual channels;

No convenient design for a 1,000 channel sequencing carrier exists at this time;

Very expensive cooled CCD arrays are required.

Potentially, the use of integrated technologies is attractive, especially when technical solutions will be found to integrate sufficiently long sequencing lanes with micro-fabricated PCR structures. Such a development appears to be yet at its infancy (Woolley et al., 1996). Thus, even though large and worthy efforts are expended on the development of ultra-multichannel integrated systems, it seems clear that the main contribution to HGP should be expected from more conventional capillary machines, based on proven technologies.

Ultimately, the increased number of lanes should be cost effective for large-scale sequencing. At this time such a trend can be seen only faintly, obscured by other factors influencing the young technology. The instrument cost per lane varies from $55,000 for the single-lane ABI-310 to approximately $3,000 per lane in ABI-377. Similar cost per lane is anticipated of the 96-capillary ABI-3700 whose expected cost is $300,000. The intermediate number for the 8-lane CEQ-2000 by Beckman-Coulter is about $9,000 per lane.

Although the trend of lower cost per lane for higher number of lanes is discernible, this trend can really be trusted only provided the increased number of lanes does not qualitatively alter the machine structure. It should be noted in this context that the transition from 100 to 1,000 lanes with the conventional methodology is fraught with many technical difficulties. Requirements become extremal on every front: ultra-fast and ultra-precise scanning; high-power laser and ultra-short observation time; beam divergence and reflections in systems with side illumination; simultaneous DNA loading and gel replacement. These technical problems may lead to a significant increase in the cost of the system and in some instances cannot be adequately addressed at all within the same methodology that works nicely for 100 channels.

It can be safely concluded that at this time there is a definite gap between the desired number (1,000) of electrophoretic channels in a high-throughput machine and the practically available number (100) that is offered by the conventional methodology. Filling this gap is the main objective of the present Proposal. Our proposed concept for the kilo-lane sequencer architecture is novel: network arrangement of asynchronous modules, optically illuminated from a common laser source via a fiber-optic network and linked to a central processing unit via an electronic network. The enabling technology for this architecture is based on the technique of single-photon detection of modulated fluorescent radiation, which has been developed in our laboratory.

The general structure of the proposed instrument is described in more detail in Sect. 4. Here we would like to list the advantageous features of the asynchronous network architecture:

Different configurations of the machine are possible, fitting specific requirements of the user;
Machine may comprise modules of different size and structure (e.g., 16-lane or 32-lane, with or without a special loading mechanism);
Like modern computer networks, the machine is readily expandable to incorporate new modules without changing the existing configuration;
Data processing can be distributed between individual modules and the CPU, permitting an hierarchical network configuration which is known to be optimal in modern network theory;
Asynchronous modular operation adds significantly to the flexibility, convenience, and reliability of the instrument;
The above list includes general features of a modular asynchronous architecture. Specific advantages, resulting from our proprietary single-photon detection technique and from the proposed fiber-optic implementation of the fluorescence-excitation network, include
Significant (more than hundred-fold) reduction in the required illumination power, thus enabling to share the output of a conventional single laser source between hundreds of individual modules;
Optical power delivered to any individual module can be varied so as to optimize the optical power distribution, depending on the task performed by individual modules;
The use of our patented modulated-excitation technique allows to work simultaneously with different sets of fluorescent dyes. Optical fiber network can deliver multiple-color excitation to any module and "color-blind" nature of single-photon detection enables detection in any range of the fluorescent spectrum.

The cost of individual modules will not exceed $5,000 and therefore the price of a 1,000 lane machine will be below $200,000. The size of individual modules will be 10×10×30 cm, giving the unit volume of about 0.1 cubic ft. The total volume of a 1,000 lane machine is about one cubic meter, nicely fitting into a laboratory space.

An important recent development has been the appearance on the market of a complete 4-color terminator labeling dye kit by Beckman-Coulter, whose excitation wavelengths are in the red/infrared range. One should expect further developments in this are. Red and infrared dye sets offer to base the DNA sequencing instrument entirely on semiconductor diode lasers—immediately, without waiting for the development of blue diode lasers. Besides the well-known general advantages of infrared sequencing, long articulated by LiCOR corporation, this development offers particular advantages for our concept of network kilo-lane machine. Fiber-optical networks have been developed by the communications industry precisely for this wavelength range, where high-quality components are readily available and inexpensive. In this context, we would like to dispel the illusion that the advent of semiconductor lasers may lead to a different architecture with individual diode laser sources in each module. Although semiconductor lasers are indeed cheap, their wavelength stabilization is not. Fiber optical distribution from a central source comprising wavelength stabilized, temperature controlled, narrow-line, efficiently driven, and modulated diode lasers will remain the optimum technical choice, both from the standpoint of cost effectiveness and reliability.

C.1. General Structure of the Kilo-lane DNA Sequencing Instrument

A block diagram of the asynchronous network instrument is shown in FIG. 1. Its basic elements are designed so as to ensure scalability of the entire structure.

Referring to FIG. 1, a block diagram of the asynchronous kilo-lane DNA sequencing instrument is shown which includes: Multicolor modulated laser source 1; Connecting optical fibers 2; Programmable fiber-optical network 3; Global computer host 4; Control signal, configuring the structure of the optical fiber network 5; Ethernet data network 6; Asynchronous 32-channel sequencing modules with single-board computer 7; Bi-directional hub 8; Switching hub 9; and Local PC host (optional) 10.

The multicolor laser source (1) [Sect.C.3] generates the optical radiation at all wavelengths required for the efficient excitation of the selected fluorescent dye set. This radiation goes to the programmable fiber-optical network (3) along optical fiber connectors (2). Similar connectors then deliver the radiation to each of N asynchronous 32-channel sequencing modules (7) [Sect.C.2.]. The minimum optical power delivered to each module is 100 $\mu$W in each wavelength component. If necessary, the illumination power can be increased for special tasks a particular module—by an automatic reconfiguring of the optical network (3), which essentially consist of optical switches and fiber splitters. The optical network configuration is managed with an electrical signal (5) from the global computer host, which controls the optical switches.

Each of the N asynchronous 32-channel sequencing modules communicates the data and receives instructions from the central computer over a standard electrical network of Ethernet type. This operating regime will be realized with the help of two network elements, the bi-directional hub (8) and the switching hub (9). The hub (8) supports the communication of all asynchronous modules (7) with the central computer host (4) while the switching hub (9) also enables interaction with the optional local PC host (10). The local host PC's may or may not be necessary. We envisage such a hierarchical unit in the case one desires to locate separate modules (or groups of modules) in different laboratories or different rooms of the same laboratory. The proposed architecture offers the possibility of such a customized local area network of modules with the local host PC's facilitating local monitoring and control, as well as display of the data.

The distributed signal processing will be organized as follows. The initial data collection, recording and preprocessing will be done on-line within the 32-channel modules, using the individual single-board computers embedded in each module [Sect.C.2.C.5]. Such single-board computers cost about $200 each. The pre-processed data will be directed to the global and/or local hosts where subsequent signal processing will produce base calls. This structure enables the optimum distribution of data processing load between the global and the local hosts. The global host computer will keep track and inform the user about the current state of each module and present all the sequencing data to the user. The global host will also do data archiving.

The described architecture that combines the fiber-optical illumination networks with the electronic network of standard Ethernet type for data handling and module control enables the implementation of a new type of sequencing machine—with the scaleable throughput and the cost per lane that decreases with increasing total number of modules. In designing the network configuration for the system, we first analyze the traffic pattern of the system. Each sequencing module is capable of processing 32 DNA sequences. Each processed sequencing lane produces approximately 1 M bit of data which is to be transferred to the host machine. The processing of each DNA sequence takes about an hour. Hence each single-board computer generates 32M bits of data per hour. Since there are 32 sequencing module, the total data to be transmitted to the computer host is about 1 G bit per hour.

Based on the above analysis, we propose to use a switching Ethernet that combines the 10-base-T(IEEE 802.3) Ethernet and 100-base-TX (IEEE 802.3U) Fast Ethernet technology. Ethernet is the most popular network as it provides a balance between speed, cost, and ease of installation. The 10-Base-T Ethernet supports data transmission up to 10M bits per second whereas the 100-Base-T counterparts supports 100 M bits per second transmission. Both the 10-Base-T and 100-Base-TX Ethernet supports the star topology and uses category 5 UTP (Unshield Twisted Pair) cable as its transmission media. We chose to use a switching rather than a shared Ethernet. This is mainly because traffic pattern is only between individual, sequencing modules and the computer host. There is no communications among the sequencing modules. The use of the switched technology allow communication packets to be stored and forwarded to the computer host rather than being broadcasted to all nodes on the network and thus eliminating unnecessary network congestion.

Having made a preliminary survey of current switching products for Ethernet, we propose to use the BayStack-303 switch by Bay Networks Inc. The BayStack-303 switch has 24 10-Base-T ports and 1 autosensing 10-BASE-T/100-Base-TX port, and 1 MDA (Media-Dependent Adapter) port. Through the use of the MDA port, we can cascade 3 BayStack 303 switches together. The 32 sequencing modules are connected to the 10-BASE-T ports, each supporting up to 10 M bits per second transmission. The computer host is connected to the 100-Base-TX port on one of the BayStack-303 switches. The higher bandwidth to the computer host has the obvious advantage of minimizing network congestion. Also, the 100-Base-TX port supports full-duplex transmission and thus allow simultaneous transmission to and from the computer host.

C.2. The 32-channel Sequencing Module

C.2.1. General Structure of the Module

Figure 2:
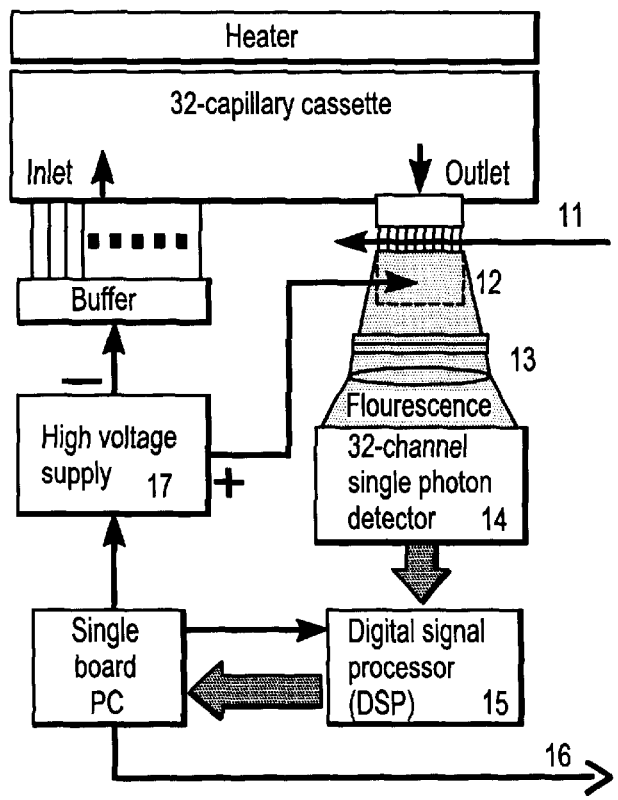
FIG. 2 is a block diagram of 32-channel module for sequencing DNA in accordance with the present invention.

Referring to FIG. 2, a block diagram of a 32-channel module for the invention is shown including Fiberized optical input 11; Detection zone of the capillary cassette 12; Optical system with filters 13; 32-channel SPDM (single-photon detection module) 14; Digital SPDM/PC interface 15; Ethernet signal output 16; and a High-voltage programmable source 17.

The module works as follows. Replaceable 32-capillary cassette is pre-charged with a polymer solution. The fluorescence-exciting illumination is delivered from outside the module via a fiberized network (11). Special micro-collimation optics directs the illumination to the detection zone (12). All 32 capillaries are illuminated simultaneously. The fluorescent radiation excited in the 32-capillary assembly is collected by the optical system (13) where the residual laser radiation is filtered out. The obtained fluorescent image is projected onto the 32-channel photomultiplier tube (PMT) which represents the optical entry port of the 32-channel SPDM, or single-photon detection module (14). Digital output of the SPDM is pre-processed by the digital interface (15) and sent to the single-board computer, which stores the information and transfers it to the user (at the local or global host) over the Ethernet. The single-board computer also controls the embedded high-voltage source (17). The use of single-board computers in a network configuration is a very cost-effective way of handling the information and controlling the units, (the alternative of arranging a full-blown PC for each module would be expensive and cumbersome). Single-board computers can operate under any of the popular OS software, such as, e.g., Windows 98) or use custom OS optimized for the data storage and processing functions specific to DNA sequencing.

C.2.2. Design and Development of the 32-channel Capillary Cassette

Figure 3:
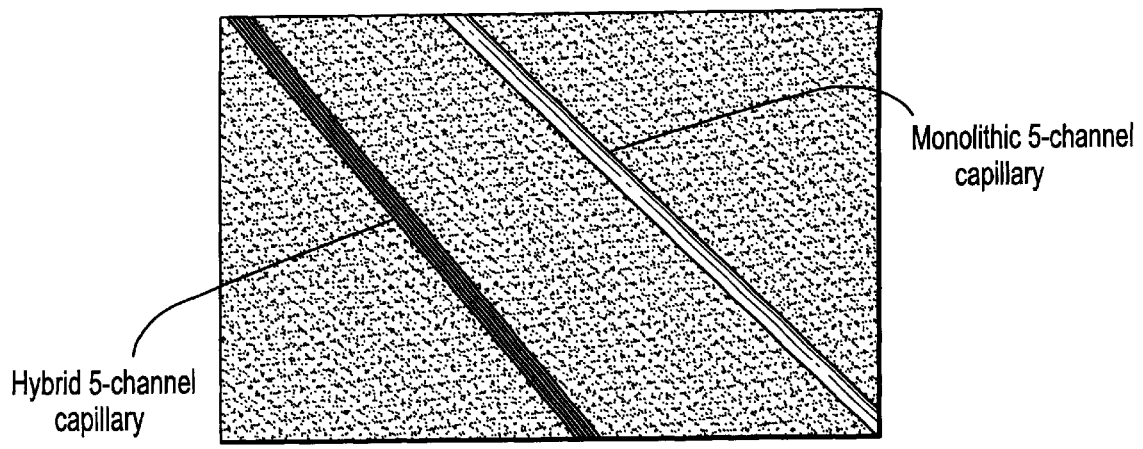
FIG. 3 depicts monolithic capillaries in accordance with the present invention.

We propose to investigate two cassette structures, that differ in the manufacturing technology and the method for sample loading. The first—low risk—version will be referred to as the hybrid cassette, the second the integral cassette. In both cassette versions the carriers of electrophoresis are capillaries of square cross-section (50 to 70 $\mu$m on the side). The hybrid version will comprise individual capillaries assembled together in a structure, that is quasi-monolithic and planar in the detection region and spaced apart in the DNA loading region. The integrated version will represent a truly monolithic 32-channel capillary manufactured as a unit by pulling a specially prepared glass ingot. Scaled down versions of both cassettes have been implemented (see FIG. 3). FIG. 3. shows multi-channel capillaries. Both the hybrid and the monolithic capillaries shown in the photograph are short sections of 60 cm-long 5-channel cassettes. Consider the two cassettes in greater detail. First let us describe the low-risk hybrid cassette.

Figure 4:
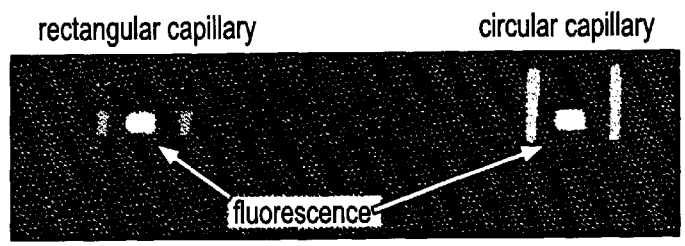
FIG. 4 depicts collimated laser light from square and round capillaries.

Hybrid 32-channel cassette represents a monolithic plate where 32 square capillaries of 60 cm length are inserted. The cassette may be filled with a heat conducting liquid. Advantage of the square capillary geometry apparent from FIG. 4. FIG. 4. shows rectangular versus circular capillaries. Passage of collimated beam of laser light across a square and circular quartz capillaries filled with a fluorescent dye solution. Strong reflections at the quartz/air boundaries in circular capillaries are eliminated in the square geometry.

On the cathode (loading) side, the 32 capillaries are arranged so as to correspond to cells of a standard 96-well plate. The loading side thus represents a 4×8 matrix of capillary edges. The separation between individual capillaries is governed by the step between cells of the standard 96 well plate.

Figure 5:
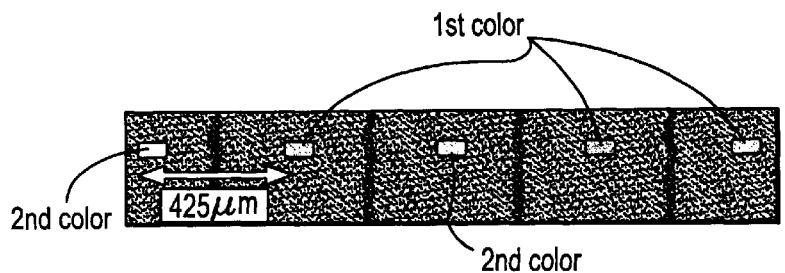
FIG. 5 depicts florescence from a 5 bundle square capillaries which show distinct colors.

On the anode side, all 32 capillaries are arranged in a coplanar way so that the illumination beam would pierce them all with a minimal reflection into the photoreceiver direction. FIG. 5 shows a photograph of the fluorescence excited in a multi-capillary assembly of square capillaries. FIG. 5 shows fluorescence excited in an assembly of 5 square capillaries, filled with fluorescent dye solutions of two distinct colors and fastened with an index-matched optical cement.

Bright fluorescent zones are clearly seen with almost invisible capillary interfaces.

Depending on the task, the hybrid 32-channel capillary cassette can either be based on replaceable capillaries (a more expensive cassette with cheap throw-away parts—capillaries only) or the entire cassette may be replaceable after a certain number of sequencing runs (cheap cassette with reusable capillaries).

An advantage of the hybrid cassette is its simple structure and geometry optimized for DNA loading from a standard 96-well plate. A possible drawback is the need for a special adjustment of the 32-channel capillary arrangement in the detection zone. However, development of the hybrid cassette contains no unproven steps and hence represents a low-risk approach.

Figure 6:
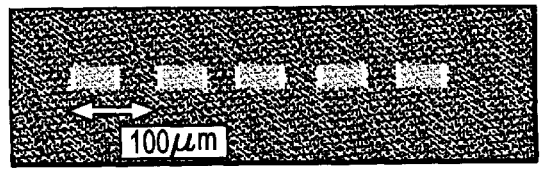
FIG. 6 shows laser light passed through a capillary filled with florescent fluid including DNA in accordance with the invention.

Integral 32-channel capillary cassette represents an integral holder for the insertion of a monolithic 32-channel capillary. Each of the channels of the 60 cm long monolithic capillary has a rectangular cross-section. We have designed and tested a 5-channel prototype of such a capillary. FIG. 6 shows the photograph of a collimated laser beam passing across the monolithic capillary filled with a fluorescent dye solution. FIG. 6 depicts a passage of laser beam across a monolithic 5-channel capillary filled with a fluorescent fluid. Bright zones of fluorescence are clearly seen with only minor internal reflection of the collimated beam inside the monolithic capillary.

The very significant advantages of the integral cassette include its low cost and the absence of any specially adjusted parts in the detection zone. Also the channel dimensions in this type of cassette can be easily harmonized with the micro-fabricated chips for DNA sample preparation, e.g., such as those described by Simpson et al (1998) and Woolley et al (1997).

Figure 7:
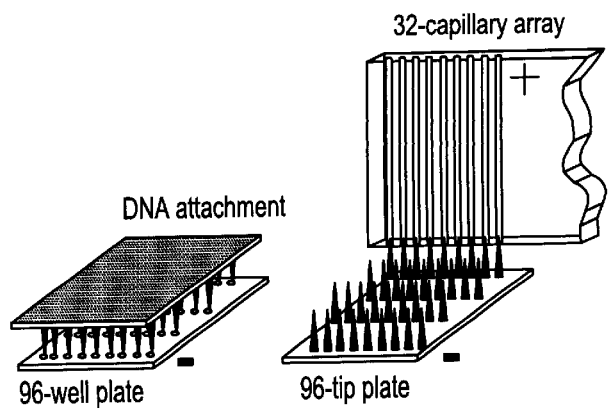
FIG. 7 shows the loading of DNA samples for a 96-well plate to the monolithic 32-channel capillary in accordance with the present invention.

The high-risk aspect of the monolithic capillary approach flows from its novelty. We need to develop a custom device for loading DNA into such a cassette. Ideally, one needs a device to connect a micro-fabricated DNA sample preparation chip (or even a pre-loaded 96-well plate) with the monolithic 32-channel capillary. This is a separate and rather complicated technical task to which the ideal solution is yet to be found. At this time we discern several approaches to be investigated. One such approach, which we currently prefer, will employ a micro-fabricated array of pyramidal silicon tips matched to the 96-well plate, as shown in FIG. 7. FIG. 7 shows the loading of DNA samples for 96-well plate to the monolithic 32-channel capillary. The array of pyramidal tips implemented on Si wafer with conventional MEMS tech-niques is dipped into a matching array of 96 wells on a standard plate. Positive voltage applied between the tips and the wells makes the DNA samples stick to the tips. The samples are then transferred and electroinjected into the monolithic array of capillaries. The positioning of the Si tip array relative to both the 96-well plate and the 32-channel capillary is effected by micro-positioners with an optical feedback. An alternative way of injecting DNA samples in a monolithic capillary may be to use micro-manipulators.

C.2.3. Illumination System for 32-channel Capillary Cassette

One of the critical issues in the development of the illumination system for a linear arrangement of 32 capillaries is the proper positioning of the detection zone relative to both the illuminator and the detector. The basic design requirements are:

high uniformity of the illumination regime for all capillaries in the detection zone;

maximum reception efficiency by each of the 32 photoreceiving channels of the fluorescent signal from the corresponding capillary channels;

In the course of this project, we shall design and implement a pilot fiberized optical system that will enable the use of 32-channel capillaries in a holder without transverse justification. This system must provide an optical beam, whose cross-section must be less than 20 $\mu$m in the capillary direction and, at the same time, must exceed the channel width by at least 5–10 $\mu$m. For a square 50×50 $\mu$m capillary, the beam transverse dimensions should therefore be at least 20×55 $\mu$m or even 15×60 $\mu$m. This calls for a rather complex astigmatic fiberized optical system.

To achieve optimum performance, we shall employ the techniques of integrated optics. Firstly, we shall develop a special integrated system that transforms the multicolor beam emerging from a single-mode optical fiber into a collimated beam with a given astigmatism in the transverse direction. Two integrated fiber optic transmitters (IFOT) will provide simultaneous bidirectional illumination at the four wavelengths of excitation of the capillary array. Each IFOT, comprising several sections of graded index and step index multi mode fibers fusion spliced together, will provide necessary wavefront processing of the laser beams launched into the single mode fiber to permit waveguiding at all four wavelengths. Under optimal conditions the illumination in the interior region of the central capillary will be better than 98% of the illumination in the end capillaries.

C.2.C. The 32-channel Single-photon-counting Photoreceiving Module

Our research in the current project (Sect.3) has clearly demonstrated the power and efficiency of single-photon counting principle in the photoreceiving unit of DNA sequencers. The 32-channel H-7620 device from Hamamatsu proved most suitable among all commercially available linear single-photon detector arrays we have analyzed. The $2,700 H-7620 offers the lowest cost per photo-receiving channel.

The counter states are read periodically and prepared for transmission to the computer. In order to permit continuous detection while transferring data to the computer, a buffer is implemented to store the data during transmission. In this way the counter states can be read and the front end can continue to monitor the detector while data is transmitted to the computer. The use of an FPGA for implementation of the buffer and computer interface gives us the flexibility to quickly adapt the system for different interfaces. Initially the read-out electronics will drive the parallel port of the computer. Future generations can be interfaced directly to the CPU (central processing unit) bus.

C.2.C.2. Electronic Data-preparation Block

This block transforms the multi channel pulse stream into a single digital stream. Each of the 32 channels comprises an 8-bit counter, which receives short pulses from the analog/digital ASIC. The 8-bit output of the counters goes to the latches and the multiplexer sequentially reads off the state of all latches and sends these to the output register. In the regime of constant count time, set by the control circuit, the system introduces practically no losses. For the count time set at 100 $\mu$sec and the duration of measurement 1 sec, the dynamic range in each channel is 2,560,000 which comfortably exceeds the dynamic range (1,000,000) of the single-photon detector itself.

Figure 8:
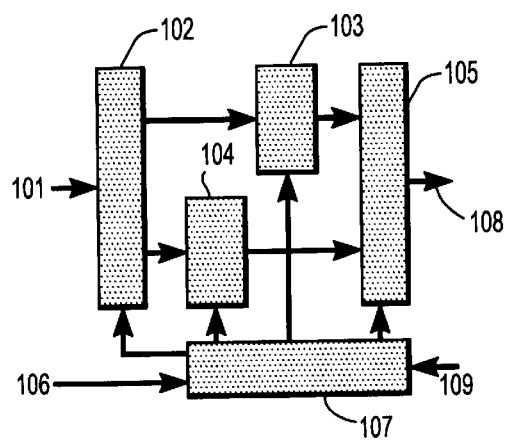
FIG. 8 is a block diagram for a digital buffer for packet data transfer in accordance with the present invention.

C.2.C3. Efficient Data Transfer Between the 32-channel SPD Head and the PC Parallel Port To organize data transfer from the 32-channel single-photon detector head to the parallel port of a PC, we shall use the technique of packet information transfer. A specially designed digital buffer will be installed between the electronic data preparation block and the parallel port, as shown in the FIG. 8. FIG. 8 shows a block diagram of the custom digital buffer for packet data transfer which includes: input data 101; demultiplexer 102; static memory block #1 103; static memory block #2 104; multiplexer 105; input synchronization signal 106; control unit 107; output data 108; and feedback signal 109. The custom buffer ensures the asynchronous operation of the data preparation block and the PC. This enhances the data transfer efficiency, which is essential for 32-channel operation. The buffer works as follows. Static memory blocks #1 and #2 (of 64 KB capacity each) are alternately connected to the input data stream. Special signal (106) synchronizes the recording with the digital circuits of single-photon detector. The alternately free memory block is connected to the PC parallel port by the control unit (107). The output data (108) are thus transferred to the PC at the rate limited only by the feedback signal (109). Evidently, the system works asynchronously if the bit rate of the parallel port exceeds that of the electronic data preparation block. The standard parallel port accepts data in 64 KB packets at the rate of up to 2 MB/sec. This corresponds to offering each of the 32 channels a bit rate capacity of 64 KW/sec, with the data organized in 8-bit words (W). This capacity is much higher than required and allows to use the remaining time resource constructively, either for preliminary data compression or for additional information channels (such as, e.g., a measure of the excitation intensity, etc.)

C.2.C.C. Data Recording and Processing

Data is transferred to a computer through a parallel port from the 32-channel electronic module. There are two general schemes to organize the recording procedure. The first scheme assumes recording of all incoming data to a storage device (hard disk) for further processing after the recording is finished. In the second scheme, the data are pre-processed in real-time and only the result is stored. Both schemes will be implemented in our machine.

The real-time processing structure is preferable where pre-processing is performed inside the electronic module. In this case, requirements on the data flow between the electronic module and the computer are significantly lower, which is of great importance for the multi-channel machine with many channels.

During preprocessing, the 32 channels must separated from incoming data and the four harmonic amplitudes must be determined for each channel. Separation of channels is realized using special codes placed in the data sequence by the electronic module. Data samples for each channel are assigned fixed positions in relation to these codes. Verification of data sequence and detection of possible errors will be implemented.

C.2.C.5. Single Board Computer Control Unit

The rapid fall of the cost of single-board computers suggests that the Control Unit can be implemented not only as an assembly of inexpensive microprocessors—but as a full-blown compact PC board. We shall be using the TX Pro II single-board computer model from ASUS Corporation. Such a device is controlled by a Pentium MMX 233 (or similar) processor and contains all necessary control units, including the high-speed parallel interface and the hard-drive controller. Thus, one inexpensive device (the total price of a single-board computer with 2 GB HD and 256 MB DRAM does not exceed $200) will fully cover our needs both for control and data recording/preprocessing. The single-board computer in each 32-channel module will effect a two-parameter (voltage and total current) control of the high-voltage source that drives capillary electrophoresis. Single-board computers will also control electromechanical components of the sequencing apparatus, based on standard step motors with a RS232 PC interface.

C.3. Multicolor Laser Source

We shall develop two types of central multicolor laser source—adapted for the excitation of ABI and Beckman-Coulter dye sets. Spectral composition and the structure of the source will be basically the same as described in Sect. 3, except that they will emit larger optical power. The required output power is estimated from the number of sequencing modules on the network and the efficiency of optical coupling and fiber splitting. For the 32-module network we need 8 splitting levels characterized by about 3 dB loss per level. To deliver the optical power of 100 $\mu$W to individual modules, the central source must be order of 100 mW. The estimated cost of ABI-oriented source based on gas lasers will be of $30,000, including the cost of network. Source oriented on red/infrared dyes will be significantly cheaper ($15,000) because of the lower cost of lasers and elimination of external choppers. Thus, with both types of sources used in the same machine, the prorated contribution of the combined central illumination source into the cost of the individual modules will be around $1,400 ($950 for blue/green source and $450 for red/infrared). When the red/infrared dyes are fully proven, the expensive blue/green optical source may be phased out. At this time, however, we believe that it must be included in the machine, because of the lack of proven record for the Beckman-Coulter dye set. In this project, we shall develop an 8-module prototype of the network machine, which requires roughly 16 times less power than the 32-module machine. Hence, to deliver 100 $\mu$W of optical power to the individual modules we shall use less expensive lasers with the output power of 10 mW. This will lower the cost of the central laser source by about factor of two.

Figure 9:
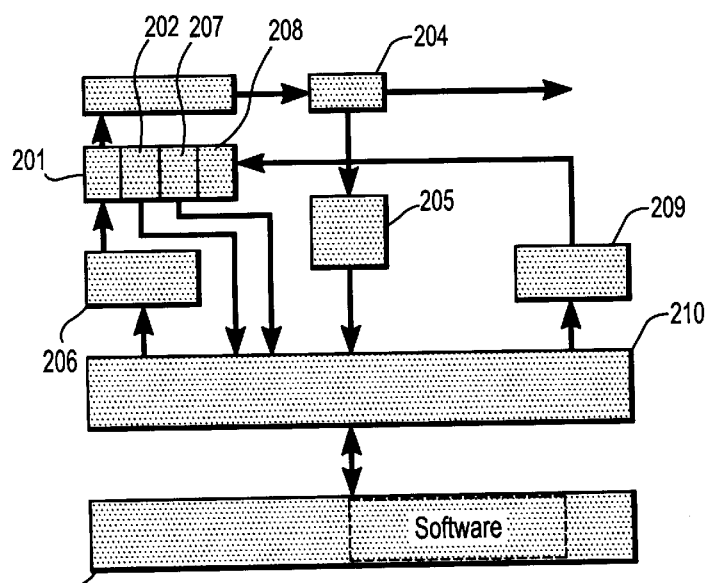
FIG. 9 is a block diagram of a stabilization system for a 4 color red/infrared laser source employed in accordance with the present invention.

Referring FIG. 9, a block diagram of the stabilization system for 4-color red/infrared laser source is shown which may include: semiconductor laser diode 201; photodiode, built in the laser 202; optical fiber network 203; 1% fiber splitter 204; common photodetector 205; current driver 206; temperature gauge 207; Peltier element 208; controllable current source 209; multichannel digital interface 210; and single-board computer 211. C.3.1. Current drivers, optical power stabilization and wavelength stabilization.

The main difference of the current drivers to be developed in this work from those already implemented, consists in the introduction of several feedback loops. Control of the driving current for each of the semiconductor diode lasers will be effected with two feedback loops: one based on a built-in photodiode at each laser, the other using the common photodetector illuminated from fiber splitter (204) that splits off 1% of the optical power. The common (for all diode lasers used) photodetector will help balance the uneven loss of optical power in different fiber couplers. The built-in photodiodes will help control the optical power of each laser and prevent destruction of lasers in case of a malfunction in the optical fiber network.

Furthermore, we shall develop a system for online monitoring of the state of the 4-color laser source. Such a system can be designed as an option in the single-board computer and conveniently realized as a digital circuit with a feedback loop. For this purpose, we plan to utilize an inexpensive multichannel ADC (analog-to-digital converter) with built-in digital and analog interfaces (Computer Boards, Inc).

Wavelength stabilization will be implemented via temperature control of laser diodes. Each diode will be supplied with a temperature gauge, a Peltier element with active heat exchange, and a controlled current source. The temperature gauge will be connected to one of the ADC inputs and the current source to one the registers of the built-in digital interface. Thus, the stabilization system will measure the temperature of each laser diode and control it (using the single-board computer) with the help of a Peltier element. In order to reject the spontaneous emission from the laser diode spectrum, we shall install 5 nm band-pass filters $10^3$:1.

C.3.2. Fiber Optic Network

This network will be implemented with a programmable optical power transfer coefficient. The basic element of the programmable network is a module comprising a combination of a fiber splitter with a fiber switch. Such a controlled module can be built on the basis of devices manufactured by 3M Corp and GOULD, Inc for computer applications. The module will one fiber input and two fiber outputs. With an electronic control the entire optical power on the input can be sent to either of the outputs or split between them. Combining such modules, we shall build a programmable network that can deliver any power cascaded in 3 dB stages down from the source laser power. We plan to develop a compact PC-controlled fiberized unit that has one fiber input and 32 fiber outputs, with programmable distribution of power between the outputs.

Figure 10:
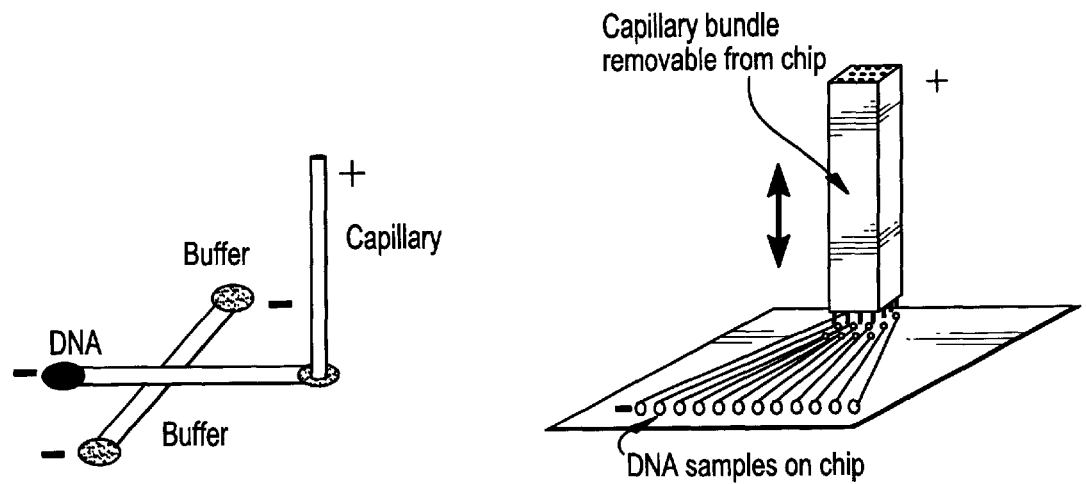
FIG. 10 is a perspective view of DNA being loaded in a capillary or capillaries in accordance with the present invention.
Figure 11:
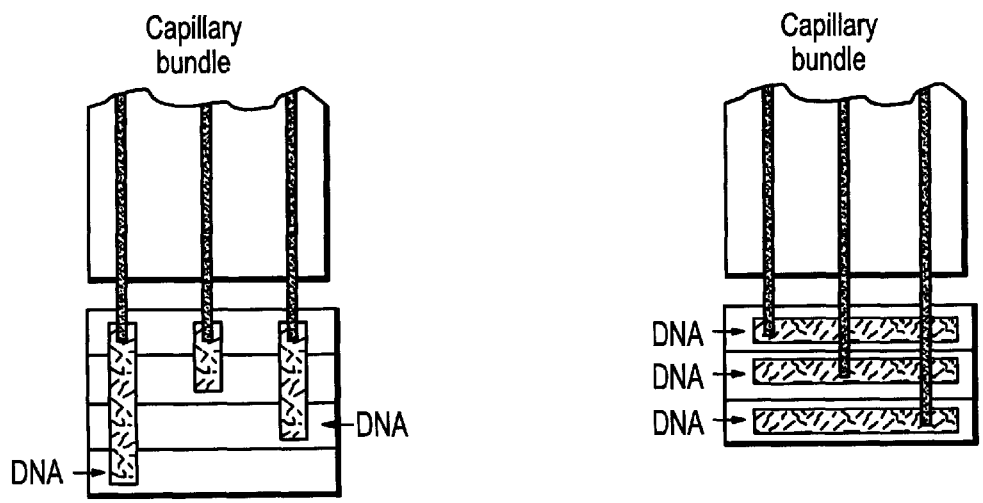
FIG. 11 is a side view showing DNA loading into capillaries of a multilayer chip in accordance with the present invention.
Figure 12:
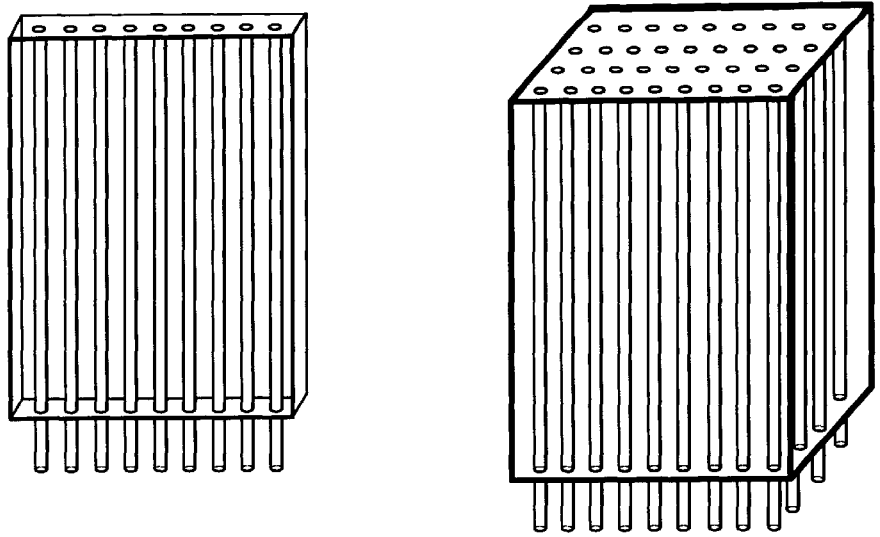
FIGS. 12 and 13 show illustrative configurations of capillary bundles in accordance with the invention.
Figure 13:
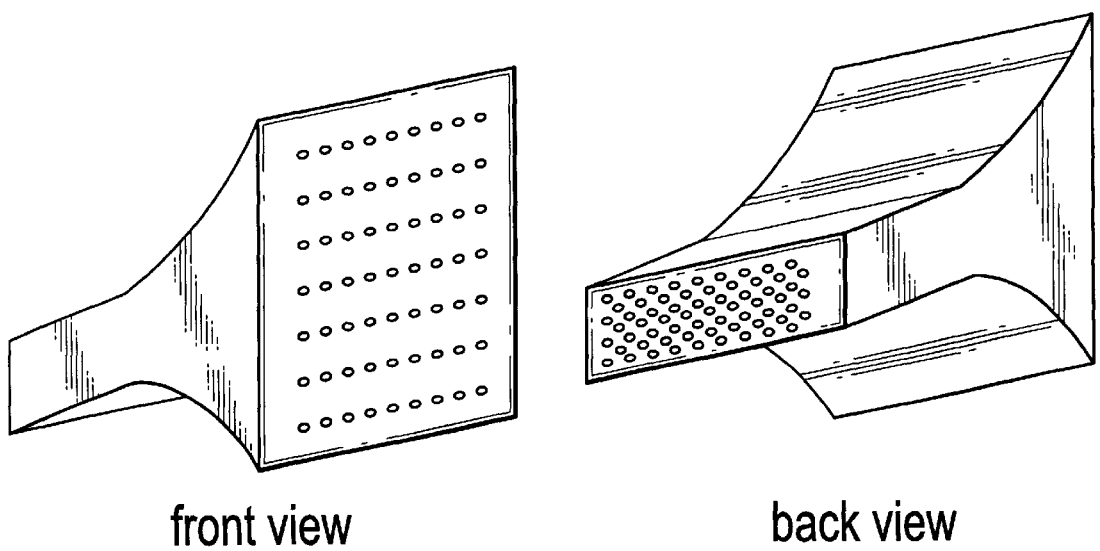

Referring to FIG. 10, a perspective view of DNA being loaded in a capillary or capillaries is shown. FIG. 11 shows DNA loading into capillaries of a multilayer chip. FIGS. 12 and 13 show illustrative configurations of capillary bundles in accordance with the invention.

Commonly assigned provisional applications U.S. Application Nos. 60/110,712 and 60/110,720 are incorporated herein by reference.

Literature Cited

Dhadwal H. S.,. Quesada M. A. and Studier W. F., (1997), DNA sequencing by multiple capillaries that form an optical waveguide,, Biomedical Optics '97, *Advances in Fluorescence Sensing Technology in Clinical Diagnostics III,* February 8–14, San Jose Khan R. R., Dhadwal H. S. and. Suh K. I., (1994), Design and characterization of integrated coherent fiber optic imaging probes, *Applied Optics,* 33:5875–5881

Quesada M. A., Dhadwal H. S., Fisk D. and Studier W. F., (1998), Multi-capillary optical waveguide system for DNA sequencing, *Electrophoresis,* 19:1415–1427

Ried, T., Baldini, A., Rand, T. C., and Ward, D. C. (1992). Simultaneous visualization of seven different DNA probes by in situ hybridization using combinatorial fluorescence and digital imaging microscopy. *Proc. Natl. Acad. Sci.* 89:1388–1392.

Simpson P. S., Roach D., Woolley A. T., Thorsen T., Johnston R., Sensabaugh G. F., (1998), Mathies R. A., High throughput genetic analysis using microfabricated96-sample capillary array electrophoresis microplates. *Proc. Nat. Acad.. Sci. USA,* 95: 2256–2261.

H. Tan, E. S. Yeung, (1998), Automation and integration of multiplex on-line sample preparation with cap[illary electrophoresis for high throughput DNA sequencing., *Anal. Chem.* 70: 4044–4053.

Woolley A. T., Mathies R. A., (1995), Ultra-high speed DNA sequencing using capillary electrophoresis chips, *Anal. Chem.* 67: 3676–3680.

Woolley A. T., Sensabaugh G. F, Mathies R. A., (1997), High speed DNA genotyping using microfabricated capillary array electrophoresis chips. *Anal. Chem.,* 69: 2181–2186.

Woolley A. T., Lao K., Glazer N., Mathies R. A., (1998), Capillary electrophoresis chips with integrated electrochemical detection, *Anal. Chem.,* 70: 684–688.

Having described preferred embodiments of a system and method of the invention (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. An electrophoresis device comprising:
   a plurality of modules comprising a plurality of electrophoretic channels adapted to separate molecules according to attributes of the molecules;
   a light source, illuminating each of the modules with light;
   a plurality of local processors, each module being connected to a local processor, wherein the local processors collect data from the modules, and the data is determined according to a change in the light source passing through a portion of the module; and
   a global processor connected to each of the local processors, the global processor adapted to present data from at least one local processor.

2. The device of claim 1, wherein the modules are asynchronous.

3. The device of claim 1, further comprising a programmable fiber-optic switch for splitting the light among the modules.

4. The device of claim 3, wherein the illumination of each module can be individually controlled by the switch.

5. The device of claim 1, further comprising at least one local host connected to at least one local processor.

6. The device of claim 5, wherein a plurality of local processors are remotely distributed.

7. The device of claim 1, further comprising a programmable fiber-optic switch for splitting the light among the modules, wherein the switch is controlled by the global processor.

8. The device of claim 1, wherein the global processor connected at least one local host, wherein each local host is connected to at least one local processor, the global processor adapted to present data from at least one module.

9. The device of claim 1, wherein the light source is a laser.

10. The device of claim 9, wherein the laser is a multicolor modulated laser.

11. The device of claim 1, further comprising a detection device for determining changes in the light.

12. The device of claim 11, wherein the detection device is a single-photon detection module.

13. An electrophoresis device comprising;
- a plurality of modules comprising a plurality of electrophoretic channels adapted to separate molecules according to attributes of the molecules;
- a laser source, illuminating each of the modules with laser light;
- a programmable fiber-optic switch for splitting the laser light among the modules;
- a plurality of local processors, each module being connected to a local processor, wherein the local processors collect data from the modules, and the data is determined according to a change in the laser light passing through a portion of the module; and
- a global processor connected to at least a local processor, the global processor adapted to present data from it least one module, and to control the programmable fiber-optic-switch.

* * * * *